(12) United States Patent
Doubler et al.

(10) Patent No.: US 9,649,135 B2
(45) Date of Patent: May 16, 2017

(54) BOTTOM LOADING LOW PROFILE FIXATION SYSTEM

(71) Applicant: Spinal LLC, Palm Beach Gardens, FL (US)

(72) Inventors: Robert L. Doubler, Monroe, MI (US); John E. Hammill, Sr., Maumee, OH (US)

(73) Assignee: Spinal LLC, Palm Beach Gardens, FL (US)

( * ) Notice: Subject to any disclaimer, the term of this patent is extended or adjusted under 35 U.S.C. 154(b) by 0 days.

(21) Appl. No.: 14/092,399

(22) Filed: Nov. 27, 2013

(65) Prior Publication Data
US 2015/0148848 A1   May 28, 2015

(51) Int. Cl.
*A61B 17/70*   (2006.01)

(52) U.S. Cl.
CPC ........ *A61B 17/704* (2013.01); *A61B 17/7037* (2013.01); *A61B 17/7049* (2013.01)

(58) Field of Classification Search
CPC .................................................. A61B 17/7037
USPC .......................... 606/264–269, 278, 304–306
See application file for complete search history.

(56) References Cited

U.S. PATENT DOCUMENTS

| | | |
|---|---|---|
| 5,545,165 A | 8/1996 | Biedermann et al. |
| 5,584,834 A | 12/1996 | Errico et al. |
| 5,628,740 A | 5/1997 | Mullane |
| 5,725,527 A | 3/1998 | Biedermann et al. |
| 5,879,350 A | 3/1999 | Sherman et al. |
| 6,050,997 A | 4/2000 | Mullane |
| 6,355,040 B1 | 3/2002 | Richelsoph et al. |
| RE37,665 E | 4/2002 | Ralph et al. |
| 6,371,957 B1 | 4/2002 | Amrein et al. |
| 6,413,259 B1 | 7/2002 | Lyons et al. |
| 6,478,798 B1 | 11/2002 | Howland |
| 6,485,491 B1 | 11/2002 | Farris et al. |
| 6,565,565 B1 | 5/2003 | Yuan et al. |
| 6,610,062 B2 | 8/2003 | Bailey et al. |
| 6,610,063 B2 | 8/2003 | Kumar et al. |
| 6,613,050 B1 | 9/2003 | Wagner et al. |
| 6,626,906 B1 | 9/2003 | Young |
| 6,916,320 B2 | 7/2005 | Michelson |
| 6,926,718 B1 | 8/2005 | Michelson |
| 6,936,050 B2 | 8/2005 | Michelson |
| 6,936,051 B2 | 8/2005 | Michelson |
| 7,008,422 B2 | 3/2006 | Foley et al. |
| 7,066,961 B2 | 6/2006 | Michelson |
| 7,105,029 B2 | 9/2006 | Doubler et al. |
| 7,118,303 B2 | 10/2006 | Doubler et al. |
| 7,334,961 B2 | 2/2008 | Doubler et al. |

(Continued)

FOREIGN PATENT DOCUMENTS

WO   WO2005018471   3/2005

*Primary Examiner* — Ellen C Hammond
*Assistant Examiner* — Stuart S Bray
(74) *Attorney, Agent, or Firm* — McHale & Slavin, P.A.

(57) ABSTRACT

A low profile orthopedic device is used to fix and stabilize bones to correct anomalies in skeletal structure occurring naturally or by trauma. Bone screws are screwed into bones by application of torque. Connectors are attached to the anchored bone screws. Each connector includes a clamp and a compression ring. A connecting rod connects several connectors together. The clamps are tightened to hold the rod to the bone screws in a pre-selected position by linear movement of the compression ring.

12 Claims, 5 Drawing Sheets

(56) References Cited

U.S. PATENT DOCUMENTS

| | | |
|---|---|---|
| 7,335,201 B2 * | 2/2008 | Doubler et al. ............... 606/264 |
| 7,438,715 B2 * | 10/2008 | Doubler et al. ................ 606/71 |
| 7,658,582 B2 | 2/2010 | Doubler et al. |
| 7,678,138 B2 | 3/2010 | Fitts et al. |
| 7,862,281 B2 | 1/2011 | Doubler et al. |
| 7,981,143 B2 | 7/2011 | Doubler et al. |
| 7,988,694 B2 * | 8/2011 | Barrus et al. ............... 606/86 A |
| RE42,867 E * | 10/2011 | Hammill et al. .............. 606/277 |
| 8,361,122 B2 * | 1/2013 | Barrus et al. .................. 606/267 |
| 8,398,683 B2 * | 3/2013 | Berrevoets et al. .......... 606/267 |
| 8,444,681 B2 * | 5/2013 | Jackson ............. A61B 17/7037 606/300 |
| 8,449,578 B2 * | 5/2013 | Keiser et al. .................. 606/264 |
| 8,491,639 B2 * | 7/2013 | James et al. .................. 606/267 |
| 8,556,938 B2 * | 10/2013 | Jackson ............. A61B 17/7008 606/264 |
| 8,613,760 B2 * | 12/2013 | Jackson ............. A61B 17/7008 606/254 |
| 8,617,217 B2 * | 12/2013 | Iott et al. ....................... 606/266 |
| 8,636,782 B2 * | 1/2014 | Biedermann ...... A61B 17/7032 606/279 |
| 8,814,919 B2 * | 8/2014 | Barrus et al. .................. 606/308 |
| 2005/0096653 A1 * | 5/2005 | Doubler ............. A61B 17/7041 606/277 |
| 2005/0228385 A1 * | 10/2005 | Iott et al. ......................... 606/61 |
| 2005/0267472 A1 * | 12/2005 | Biedermann et al. .......... 606/61 |
| 2005/0277928 A1 | 12/2005 | Boschert |
| 2006/0173456 A1 * | 8/2006 | Hawkes et al. ................. 606/61 |
| 2006/0241600 A1 | 10/2006 | Ensign et al. |
| 2007/0093817 A1 * | 4/2007 | Barrus ............... A61B 17/7032 606/264 |
| 2008/0004625 A1 | 1/2008 | Runco et al. |
| 2008/0009862 A1 | 1/2008 | Hoffman |
| 2008/0027432 A1 * | 1/2008 | Strauss ............... A61B 17/7032 606/279 |
| 2008/0154315 A1 | 6/2008 | Jackson |
| 2008/0249576 A1 * | 10/2008 | Hawkes et al. ................ 606/305 |
| 2009/0105716 A1 * | 4/2009 | Barrus ............... A61B 17/7032 606/301 |
| 2009/0105769 A1 * | 4/2009 | Rock .................. A61B 17/7032 606/308 |
| 2009/0292308 A1 * | 11/2009 | Jones ................. A61B 17/7032 606/205 |
| 2010/0114170 A1 * | 5/2010 | Barrus ............... A61B 17/7037 606/264 |
| 2010/0114171 A1 * | 5/2010 | Boachie-Adjei ... A61B 17/7008 606/264 |
| 2010/0114180 A1 * | 5/2010 | Rock .................. A61B 17/7037 606/308 |
| 2010/0262196 A1 * | 10/2010 | Barrus ............... A61B 17/7037 606/308 |
| 2011/0208248 A1 * | 8/2011 | Barrus ............... A61B 17/7032 606/305 |
| 2011/0276093 A1 * | 11/2011 | Barrus et al. .................. 606/264 |
| 2013/0110179 A1 * | 5/2013 | Barrus et al. .................. 606/305 |
| 2014/0058451 A1 * | 2/2014 | Iott et al. ....................... 606/266 |
| 2014/0088650 A1 * | 3/2014 | Taddia et al. .................. 606/267 |
| 2014/0094853 A1 * | 4/2014 | Iott et al. ....................... 606/266 |
| 2016/0262816 A1 * | 9/2016 | Doubler ............. A61B 17/8605 |

\* cited by examiner

BOTTOM LOADING LOW PROFILE FIXATION SYSTEM

FIELD OF THE INVENTION

This invention relates to orthopedic surgery and, in particular, to a bottom loading low profile fixation system.

BACKGROUND OF THE INVENTION

Chronic back problems are caused by intervertebral disc disease and deterioration and loss of stability of the intervertebral joints. Examples of these spinal conditions include degenerative disc disease, scoliosis, spondylolithesis, spinal stenosis, etc. Stabilization and/or arthrodesis of the intervertebral joint can reduce the pain associated with movement of a diseased or deteriorated intervertebral joint. In order to allow for development of a solid intervertebral fusion, the spine has to be stabilized. Severe trauma to the back can further cause conditions wherein the spine needs to be stabilized. There are many instances in which it is necessary to stabilize and fix bones and bone fragments in a particular spatial relationship to correct the location of skeletal components due to injury or disease. One group of devices employ a number of bone screws placed across a discontinuity in adjacent vertebrae and connected by a rod to maintain a predetermined spatial location.

Spinal stabilization systems have been developed to stabilize the vertebrae to allow for fusion or stabilization of diseased intervertebral joints. One type of spinal stabilization system includes connectors and rods that are used to stabilize the spine. Some examples of such spinal stabilization systems are disclosed in U.S. Pat. Nos. 6,613,050; 6,371,957; 6,050,997; 5,879,350; 5,725,527; 5,628,740; and 5,545,165, the disclosures of which are incorporated herein by reference. In these systems, connectors are anchored to the vertebral bodies desired to be stabilized by anchoring structures such as screws or hooks. One or more connecting rods are then secured to the connectors to form a connector/rod construct that stabilizes the vertebral bodies to which the connectors are secured.

In many known stabilization systems, threaded nuts are used to secure the rods to the connectors. The rods can be provisionally held in position by loosely tightening the nuts on the connectors. After desired adjustments are made with respect to the relative positioning of the bones desired to be stabilized, the nuts can be further tightened to finally secure the connector/rod construct. Typically, a torque wrench or similar device is used to achieve the required torques to finally secure the connector/rod construct. To prevent torque from being transferred to the patient while tightening the nut, an anti-torque device is frequently used in combination with the torque wrench. The effective use of the torque wrench and anti-torque device can be difficult and often is dependent upon the strength and experience of the surgeon. The inventors torqueless fasteners patents include U.S. Pat. Nos. 7,105,029; 7,118,303; 7,334,961; 7,335,201; 7,438,715; 7,658,582; 7,678,138; 7,862,281; 7,981,143 and RE42,715, the entire disclosures of which are incorporated herein by reference.

U.S. Pat. No. 6,626,906 issued Sep. 30, 2003 to Young teaches a spinal rod attached to a spinal anchor by a clamp. The clamp is tightened about the anchor by a collet screwed into the clamp. The rod is held in the clamp by a split ring that is reduced in size by the collet. The anchor is placed in the bone by torque and the collet is tightened by additional torque.

U.S. Pat. Nos. 6,610,063; 6,610,062; 6,565,565; RE 37,665; 6,478,798; 5,584,834 teach various spinal rod coupling devices that are secured to bone screw anchors by clamps that require additional torque to be applied to the assembly after the bone screw has been seated in the bone.

In normal practice, the bone screws are each anchored in the bone with a specific amount of torque that approaches the ultimate sustainable force between the screw threads and the bone. The bone screws are then connected together by a rod having sufficient stiffness to maintain the desired skeletal orientation. The connection between the rod and the bone screws must be strong enough to be immobile. Alternatively, a torqueless connector is coupled to a bone screw, wherein the bone screw is installed in combination with the connector.

All these prior art spinal fixation devices result in additional torque applied to the assembly, and thereby to the bone screw, to tighten and lock the rod to each of the bone screws. The additional load may strip the purchase between the bone and the threads of the bone screw. To prevent such a result, some tool must be used to counter the torque of locking the rod and the screws. The use of an anti-torqueing tool requires additional coordination by the surgeon or surgeons to prevent slippage.

What is needed in the art is a system for connecting a rod to an embedded bone screw using compressive forces rather than torque.

SUMMARY OF THE PRESENT INVENTION

The present invention provides a linear locking set screw system capable of rapid linear engagement of a bone screw and a rod. Bone screws are screwed into bones by application of torque, the top of each bone screw having a spherical head. A connector is attached to the head of each of the anchored bone screws. Each connector includes a clamp body having a rod slot section and a receptacle section for placement over the spherical head. A compression ring is placed around the clamp body. A connecting rod connects several connectors together upon placing the rod within the rod slot. The clamps are tightened to hold the rod to the bone screws in a pre-selected position by linear movement of the compression ring.

It is an objective of the present invention to provide a low profile spinal stabilization system capable of precise and reproducible linear engagement and disengagement.

Still another objective of the present invention is to provide a connector that provides a bottom loading low profile spinal stabilization system, the connector being attached to a bone screw after the bone screw has been anchored.

Yet another objective of the present invention is to provide a low profile spinal stabilization system capable of locking a spinal connecting rod to an anchored bone screw by linear engagement so as to eliminate torque fastening.

Yet a further objective of the present invention is to teach the use of a linear fastener that is adjoined to an anchored bone screw for support of ancillary devices adapted to be secured together without rotational torque forces.

Other objectives and advantages of this invention will become apparent from the following description taken in conjunction with the accompanying drawings which set forth, by way of illustration and example, certain embodiments of this invention. The drawings constitute a part of

DETAILED DESCRIPTION OF THE INVENTION

Figures 1, 2:
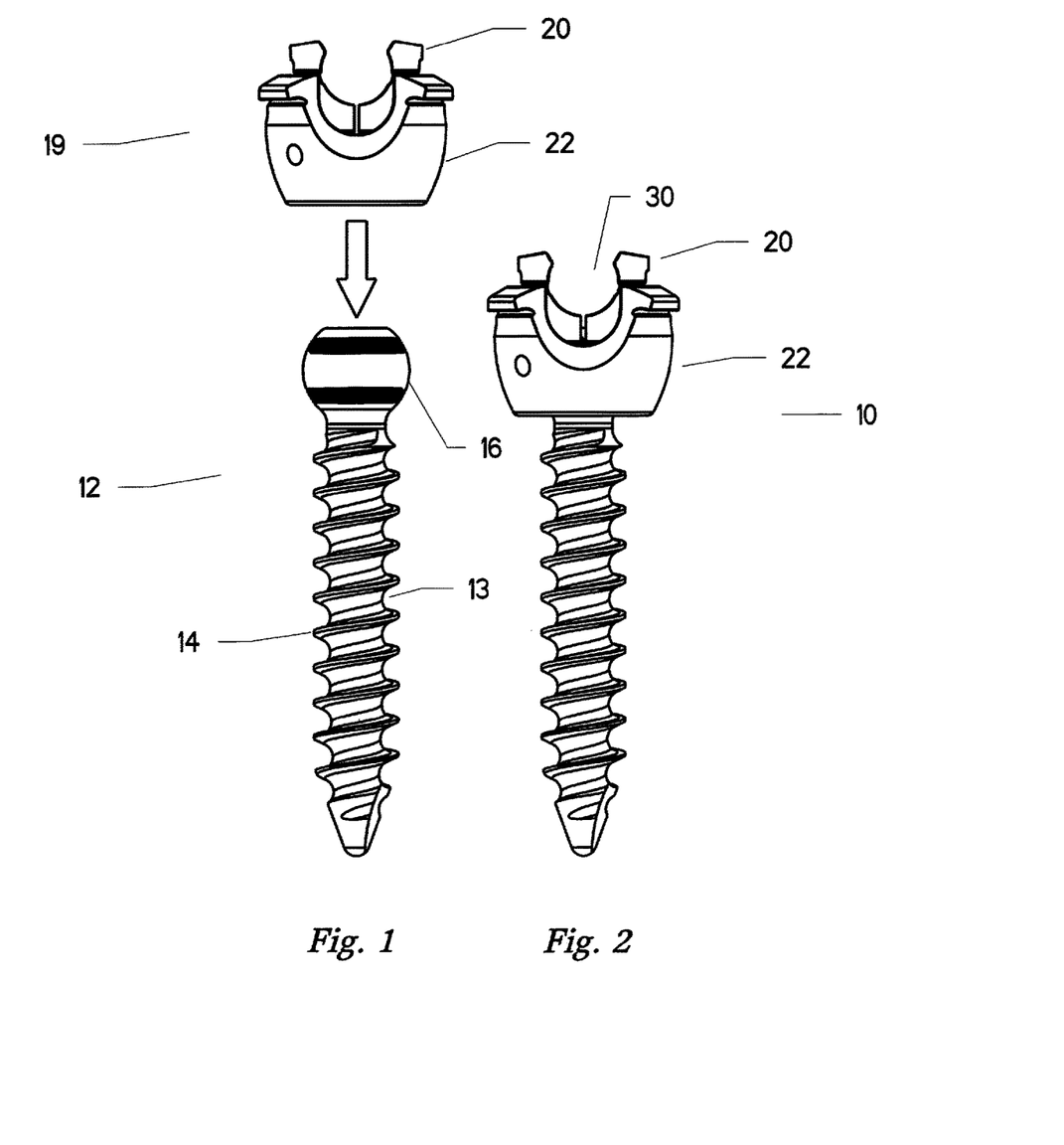
FIG. 1 is an exploded view of the bottom loading orthopedic device of the instant invention.
FIG. 2 is a plane view of the device with the connector coupled to the bone screw.
Figures 3, 4:
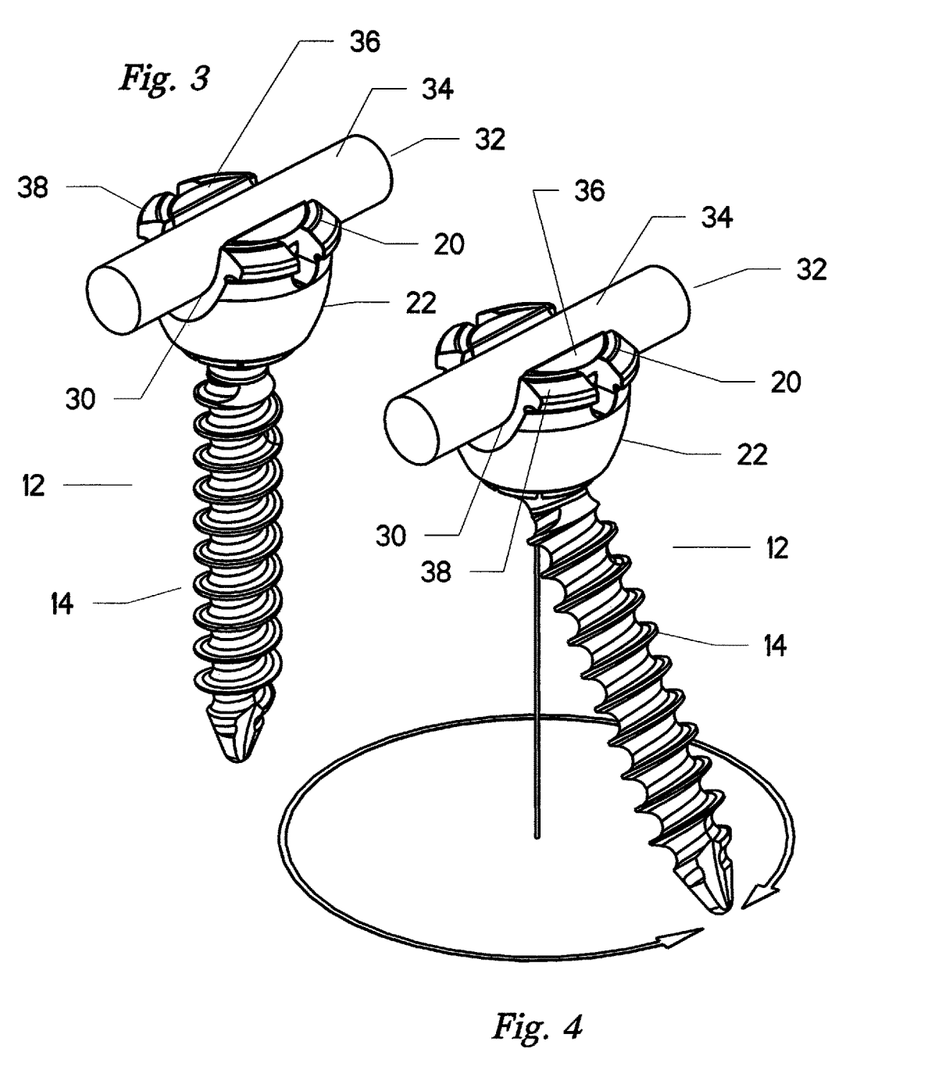
FIG. 3 is a plane view of the device locked to a rod providing a vertical low profile vertical stance.
FIG. 4 is a plane view of the device locked to a rod providing an angular low profile stance.
Figure 5:
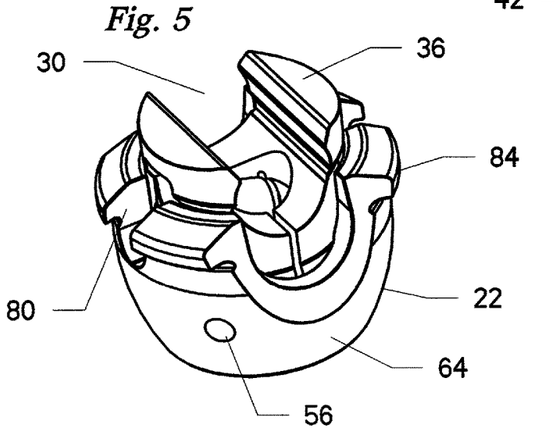
FIG. 5 is a perspective view of the connector.
Figures 6, 7:
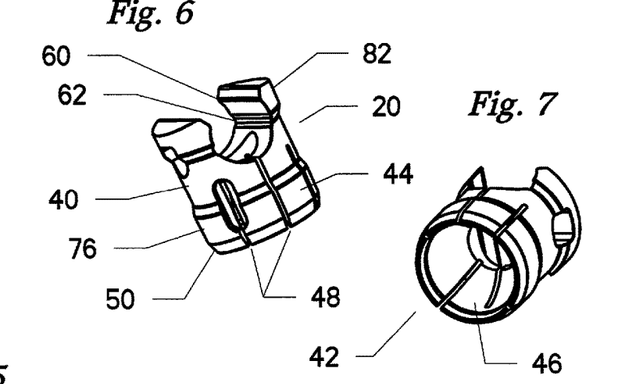
FIG. 6 is an upper perspective view of the clamp portion of the connector.
FIG. 7 is a lower perspective view of FIG. 6.
Figure 8:
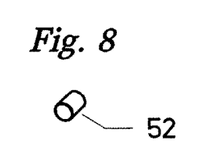
FIG. 8 is a perspective view of a pin used to secure the clamp to the compression ring.
Figures 9, 10:
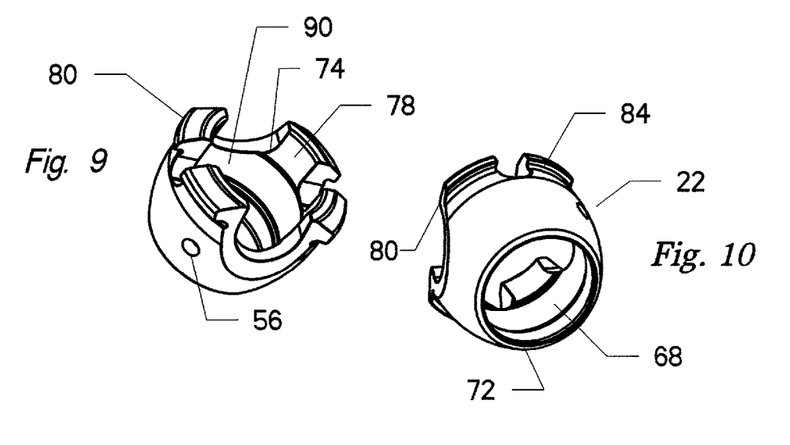
FIG. 9 is an upper perspective view of the compressing ring portion of the connector.
FIG. 10 is a lower perspective view of FIG. 9.

Referring now to the Figures, set forth is an orthopedic fixation device 10 for use in stabilizing and fixing the vertebra in relation to each other and the sacrum. The fixation device 10 employs a bone screw anchor 12 having an exterior helical threaded shank 14 to gain purchase in the cancellous bone through application of torque. A spherical head 16 is formed at the top of the helical threaded shank 14 which is constructed and arranged for bottom loading into a connector 19 formed from a clamp 20 positioned within compression ring 22. A recess 24 is formed in the top of the bone screw anchor 12 to permit installation of the bone screw anchor into cancellous bone by rotation. A torque is applied to the bone screw anchor by the surgeon using a tool (not shown) that engages the recess 24 in the head 16 and rotates the screw about its longitudinal axis. The amount of torque is critical to installation and the long life of the prosthesis in that too little does not secure the screw from loosening or backing out, and too much causes the stripping of the thread path in the bone and loss of purchase. The surgeon attempts to apply the optimum torque when placing the screws in the bone and additional torque on the bone screw is to be avoided. FIG. 1 illustrates an exploded view with the bone screw anchor 12 of head 16 exposed and available for receipt of the clamp 20 and compression ring 20. FIG. 2 illustrates the bone screw anchor 12 upon receipt of the clamp 20 and compression ring 22, a rod slot 30 is available for receipt of a rod. As illustrated, a first position is formed wherein the clamp 20 is placed over the spherical ball 16 and is available for receipt of a rod into the rod slot 30. The spherical ball 16 is frictionally engaged by a lower end of the clamp 20, to be further explained later in this specification, providing a sufficient interference fit to maintain the rod slot 30 in a position that can be directed by the surgeon awaiting receipt of the rod. FIG. 3 illustrates the bone screw anchor 12 in a vertical stance with a rod 32 placed within the rod slot 30 and the clamp 20 drawn into the compression ring 22, locking the rod 32 in fixed position in relation to the bone screw anchor 12. FIG. 4 illustrates the bone screw anchor 12 in an angular stance with a rod 32 placed within the rod slot 30 and the clamp 20 drawn into the compression ring 22, locking the rod 32 in fixed angular position in relation to the bone screw anchor 12. The spherical head 16 of the bone screw anchor 12 provides polyaxial movement of the clamp 20 and compression ring 22. During the spinal fixation, several bone screw anchors are threaded into the different vertebrae according to the anatomy of each vertebra. This results in a series of bone screw anchors without uniformity in angle or alignment. To compensate for these anomalies, the connection between the head of the screw anchors and the clamp bodies pivots or swivels to capture a connector rod. FIGS. 3 and 4 illustrate how the screw anchors can be positioned in relation to the clamp bodies. Further, the low profile stance is illustrated wherein the upper edge 34 of the rod 32 is locked in a position wherein the clamp top surface 36 is in a similar plane as the compression ring top surface 38.

The clamp body 20 is generally tubular, forming a receptacle section 42 at one end and a rod slot 30 at the other end. The receptacle is of a size to accommodate the head 16 of the bone screw anchor with a wall 40 formed by an outer wall surface 44 having a cylindrical shape and an inner wall surface 46 of a conical shape for capturing the head 16 upon insertion. A series of circumferential slots and relief slits 48 are constructed and arranged to increase the radial flexibility of the wall 40 along the receptacle section 42 in response to the curvature of the compression ring 22. The slot 30 has an upper longitudinal ridge 60 and a lower longitudinal ridge 62 to grip the connector rod 32. A lip 50 is formed along the lower edge of the receptacle section 42 outer wall surface 44. The outer wall surface 44 of clamp 20 may be tapered or otherwise shaped to provide a change in external diameter along the length.

The compression ring 22 is force fit on the wall 40 of the clamp 20 by flexing the tubular walls. The compression ring 22 is movable along the outer surface wall 44 from an open position to a closed position. The open position, as shown in FIG. 2, allows swiveling movement of the bone screw anchor head 16 and sliding movement of the connector rod 32 within the clamp 20. In the closed position, shown in FIGS. 3 and 4, the compression ring 22 applies compressive forces between the clamp 20 and the rod 32, and between the clamp 20 and the bone screw anchor 12. The compression ring 22 has a shaped inner surface 68 with a lower annular ridge 72 and an upper annular ridge which engages the lip 50 and annular bulge 76, respectively, on the outer wall surface 44 of the clamp 20 in the closed position. In addition, the compression ring 22 includes an annular surface 78 formed along compression fingers 80 for engaging the upper bulge 82 formed along the outer side surface of the clamp in the closed position. The clamp 20 is preinstalled in the compression ring 22 and a pin 52 is placed within receptacle 56 of the compression ring 22 to maintain the clamp 20 within the compression ring. The pin operates as an interference fit to prevent the clamp 20 from disengaging the compression ring 22 while the head 16 of the bone screw anchor is installed.

Figure 14:
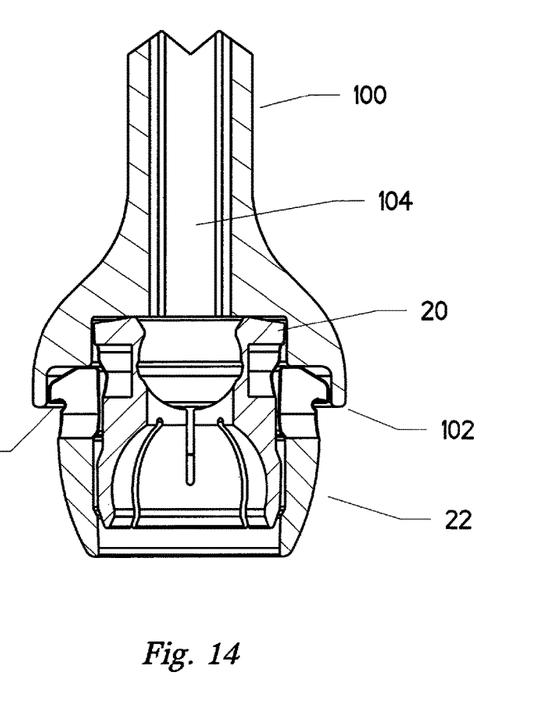
FIG. 14 is a cross sectional view of an installation instrument secured to the orthopedic device.
Figure 15:
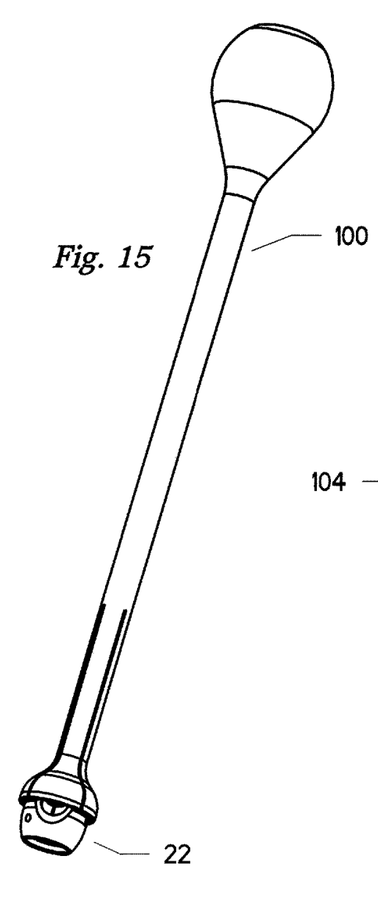
FIG. 15 is a perspective view of an installation instrument of FIG. 14.

The application of the compressive force that immobilizes the components of the orthopedic device is generated by a linear movement of the compression ring relative to the exterior walls of the clamp. This movement to the closed position is accomplished using a simple telescoping instrument 100 engaging the clamp 20 and the compression ring so that equal and opposite forces move the ring without imparting stress to the anchored screw. Instrument 100 includes an inwardly facing lip 102 for engaging an outwardly projecting tab 104 to pull up on the compression ring 22 at the same time an insertion tap 104 places an equal and opposite force onto the rod, not shown in FIG. 14, forcing the clamp 20 into the compression ring 22 for locking the rod and bone screw anchor in position. In the event of remedial surgery, the clamp may be moved to the open position in the same manner.

Figure 11:
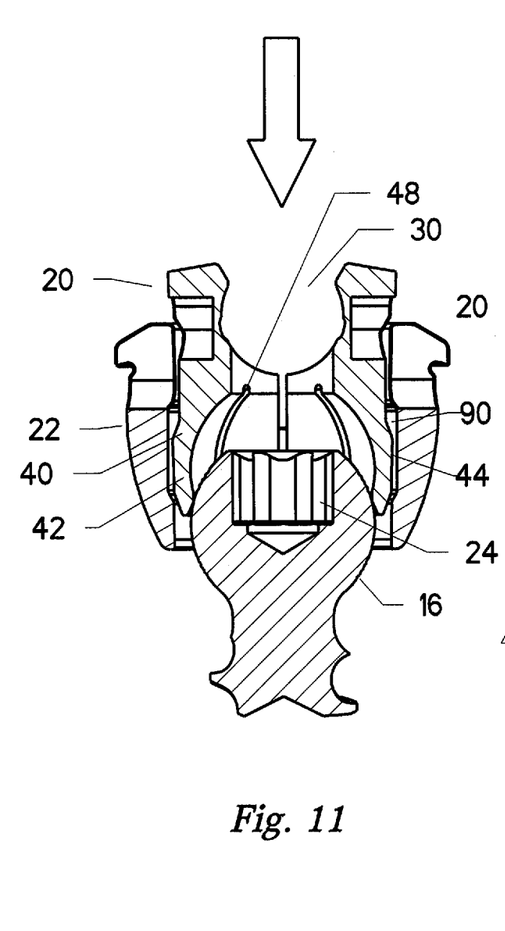
FIG. 11 is a cross sectional view of the connector before attachment to a bone screw.
Figure 12:
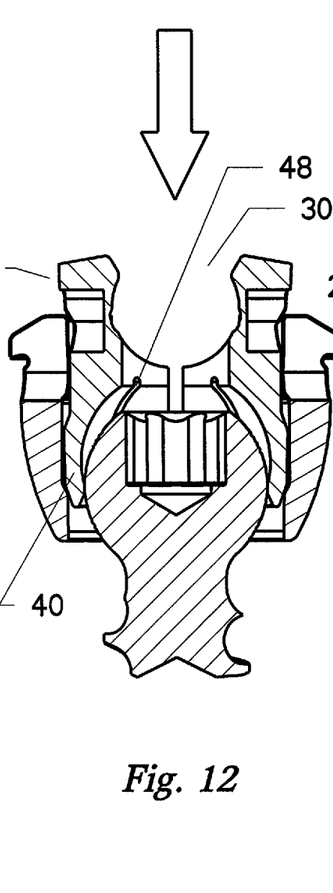
FIG. 12 is a cross sectional view of the connector during attachment to the bone screw.
Figure 13:
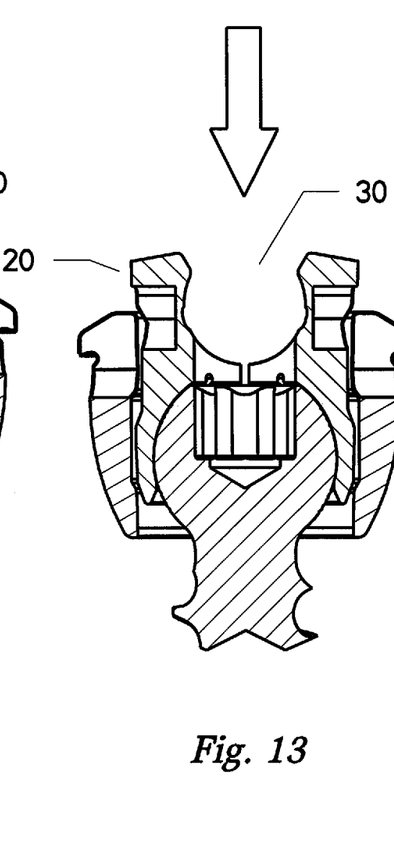
FIG. 13 is a cross sectional view of the connector after attachment to the bone screw.

FIG. 11 depicts the clamp body 20 assembled to the compression ring 22. The receptacle section 42 is available for receipt of the head 16. The receptacle section includes the wall 40 having a cylindrical shaped outer wall surface 44 that is enlarged along a length and expandable into an inner wall surface 90 of the compression ring 22. As illustrated in FIG. 12, the series of circumferential slots and relief slits 48 increase the radial flexibility of the wall 40 along the receptacle section 42 in response to the curvature of the head 16 as it pushes apart the lip 50 of the clamp body 20 into the inner wall surface 90 of the compression ring 22. FIG. 13 depicts the head 16 within the receptacle section 42, the wall 40 now encompasses the head 16 with the outer wall surface 44 restored to a biased position around the head 16. The rod slot 30 is now available for positioning by the surgeon, the head 16 is in frictional contact with the clamp 20 wherein the clamp 20 can be placed in any angular position and held in position for receipt of a rod. Once a rod is inserted into the rod slot, the compression ring 22 is lifted up while the clamp 20 is pushed down to provide a low profile locked rod as illustrated in FIGS. 3 and 4.

The instant invention provides an orthopedic kit for stabilizing bones wherein at least one bone screw 12 having a first end constructed and arranged as a shank portion 13 for penetrating securement to a bone and a second end constructed and arranged as a head portion 16. The connector 19 is used for securing a rod to a plurality of anchored bone screws, the connector 19 is formed from a clamp 20 universally connected to the head portion 16 of each anchored bone screw 12 for securing the anchored bone screw to a rod 32. The clamp 20 has an elongated body with an exterior wall 40 with a first annular bulge 76, and a rod slot 30 extending across the exterior wall constructed and arranged to slidably accept the rod 32. A compression ring 22 surrounding the exterior wall of the clamp 20, the compression ring linearly traversable along the exterior wall 40 between a first position and a second position by a force consisting of a linear force along a longitudinal axis of the clamp 20; the first position permitting adjustment of the rod as depicted in FIGS. 2 and 13, and the second position compressing the clamp 20 to immobilize the rod 32 with respect to the bone screw 12 as depicted in FIGS. 3 and 4. Traversal of the compression ring 22 from the first position to the second position causes the compression ring 22 to cooperate with the annular bulge 76 to apply compressive forces to the clamp 20 to immobilize the connections between the clamp 20 and the rod 32, and the clamp 20 and the anchored bone screw 12. The annular bulge 76 is positioned along a length of the exterior wall 40 of the clamp thereof to provide a change in the external diameter of the clamp; the annular bulge 76 constructed and arranged to cooperate with the compression ring 22 to apply compressive forces to the clamp 20 for immobilizing the connections between the clamp and the anchored bone screw head 16.

The exterior wall 40 of the clamp 20 includes a second bulge 82 to provide a change in the external diameter along the upper edge of the exterior wall. The annular bulge is constructed and arranged to cooperate with the compression ring 33 to apply compressive forces to the clamp 20 for immobilizing the connections between the clamp and the rod using ridges 60 and 62 for additional compressive force.

The first bulge 76 is constructed and arranged to cooperate with a lower annular ridge 72 while the compression ring 22 is in the second position to immobilize the connection between the clamp 20 and the anchored bone screw head 16.

A method is further disclosed of using the orthopedic device to stabilize bones across a discontinuity, comprising: providing at least two bone screws having a threaded shaft and a spherical head; anchoring said bone screws into a bone by rotation of each screw into bone; providing a connector having a clamp body and a compression ring, said clamp body having a spherical head receptacle at one end and a rod slot at an opposing end, the receptacle sized to accommodate the head of the bone screw, the compression ring having an exterior wall movable along an exterior wall of the clamp body between an open position and a closed position, the compression ring including an annular flange at the upper edge thereof, the open position defined when the first compression ring is adjacent the receptacle such that the bone screw is pivotable relative to the clamp body; placing a rod member slot whereby the rod member extends across a discontinuity; and repositioning the first compression ring from its open position to its closed position by applying a linear force along the longitudinal centerline of said clamp for traversing said compression ring to a closed position along said exterior wall of said clamp member to compress said second clamp member to substantially fix said clamp member and said rod member in a predetermined orientation with respect to the anchored bone screw whereby said bones are stabilized across said discontinuity.

The method includes providing bone screws with an external helical thread, applying torque to the threaded bone screws for anchoring into bone, and moving the compression ring linearly by application of equal and opposite forces.

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An orthopedic device for stabilizing bones comprising: a bone screw having a first end and a second end, said first end constructed and arranged as a shank portion for penetrating securement to a bone, said second end constructed and arranged as a head portion; a connector for securing a rod to an anchored bone screw, said connector consisting of a clamp and a compression ring wherein said clamp is positioned within said compression ring, and securable to said head portion of said anchored bone screw, said clamp having an elongated body with an exterior wall, said exterior wall including at least one annular bulge to provide a change in the external diameter of said exterior wall and a second bulge distal to said at least one annular bulge wherein the second annular bulge forms a receptacle section and is of a size to accommodate the head of the bone screw anchor whereby said head portion of said bone screw head is inserted therethrough, a rod slot extending across said exterior wall constructed and arranged to accept said rod, and a compression ring surrounding said exterior wall, said compression ring linearly traversable along said exterior walls between a first position and a second position by application of a force consisting of a linear force along a longitudinal axis of said clamp, whereby traversal of said compression ring from said first position to said second position causes said compression ring to cooperate with said at least one annular bulge to apply concurrent compressive forces to said clamp to simultaneously immobilize movement between said clamp and said rod and said clamp and said anchored bone screw.

2. The orthopedic device for stabilizing bones of claim 1 wherein said compression ring includes at least one inner annular ridge constructed and arranged to engage said at least one annular bulge in an overlapping manner while said compression ring is in said second position, whereby engagement of said at least one bulge and said at least one ridge applies compressive forces to said clamp for immobilizing said clamp to said head of the anchored bone screw.

3. The orthopedic device for stabilizing bones of claim 1 wherein said compression ring includes one inner annular surface constructed and arranged to engage said at least one annular upper bulge in an overlapping manner while said compression ring is in said second position, whereby engagement of said at least one annular upper bulge and said at least one annular surface applies compressive forces to said clamp for immobilizing said clamp to said rod.

4. The orthopedic device for stabilizing bones of claim 1 wherein said at least one annular bulge is constructed and arranged to cooperate with said compression ring to apply compressive forces to said clamp for immobilizing connections between said rod and said anchored bone screw.

5. The orthopedic device for stabilizing bones of claim 1 wherein the at least one annular bulge is constructed and arranged to cooperate with said compression ring while said compression ring is in said second position to immobilize the connection between said clamp and said bone screw said second bulge constructed and arranged to cooperate with said compression ring to immobilize the connection between said clamp while said compression ring is in said second position, whereby said compression ring may independently engage said first or said second bulges during translation thereof.

6. The orthopedic device for stabilizing bones of claim 1 wherein said bone screw includes at least one helical thread for penetrating and engaging a bone and wherein said head portion is at least partially spherical in shape.

7. An orthopedic kit for stabilizing bones comprising: at least one bone screw having a first end and a second end, said first end constructed and arranged as a shank portion for penetrating securement to a bone, said second end constructed and arranged as a head portion; a connector for securing a rod to a plurality of anchored bone screws, said connector consisting of a clamp and a compression ring wherein said clamp is positioned within said compression ring, and universally connected to said head portion of each said anchored bone screw for securing said anchored bone screw to a connector rod, said clamp having an elongated body with an exterior wall with an annular bulge and a second bulge distal to said annular bulge wherein the second annular bulge forms a receptacle section and is of a size to accommodate the head of the bone screw anchor wherein said head portion of said bone screw head is inserted, a rod slot extending across said exterior wall constructed and arranged to slidably accept said rod, and a compression ring surrounding said exterior wall of said clamp, said compression ring linearly traversable along said exterior wall between a first position and a second position by a force consisting of a linear force along a longitudinal axis of said clamp, said first position permitting adjustment of said rod, said second position compressing said clamp to immobilize said rod with respect to said bone screw; whereby traversal of said compression ring from said first position to said second position causes said compression ring to cooperate with said annular bulge to apply concurrent compressive forces to said clamp to simultaneously immobilize movement between said clamp and said rod and said clamp and said anchored bone screw.

8. The orthopedic kit for stabilizing bones of claim 7 wherein annular bulge is positioned along a length of said exterior wall of said clamp thereof to provide a change in the external diameter of said clamp, said annular bulge constructed and arranged to cooperate with said compression ring to apply compressive forces to said clamp for immobilizing movement between said clamp and anchored bone screw head.

9. The orthopedic kit for stabilizing bones of claim 7 wherein said exterior wall of said clamp includes a second annular bulge to provide a change in the external diameter along the upper end of said exterior wall, said second annular bulge constructed and arranged to cooperate with said compression ring to apply compressive forces to said clamp for immobilizing the movement between said clamp and said rod.

10. The orthopedic kit for stabilizing bones of claim 9 wherein said bulge is constructed and arranged to cooperate with a lower annular ridge while the compression ring is in the second position to immobilize the connection between the clamp and the anchored bone screw head.

11. The orthopedic kit for stabilizing bones of claim 7 wherein said first end of said bone screw includes at least one helical thread for penetrating and engaging a bone.

12. The orthopedic kit for stabilizing bones of claim 7 wherein said head portion of said bone screw is substantially spherical in shape.

\* \* \* \* \*